(12) United States Patent
DeLuca et al.

(10) Patent No.: US 7,763,598 B2
(45) Date of Patent: *Jul. 27, 2010

(54) 1α-HYDROXY-2-(3'-HYDROXYPROPYL-IDENE)-19-NOR-VITAMIN D COMPOUNDS WITH A 1,1-DIMETHYLPROPYL SIDE CHAIN

(75) Inventors: Hector F. DeLuca, Deerfield, WI (US); Agnieszka Glebocka, Madison, WI (US); Rafal R. Sicinski, Warsaw (PL); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 398 days.

This patent is subject to a terminal disclaimer.

(21) Appl. No.: 11/697,430

(22) Filed: Apr. 6, 2007

(65) Prior Publication Data

US 2007/0238703 A1   Oct. 11, 2007

Related U.S. Application Data

(60) Provisional application No. 60/791,487, filed on Apr. 10, 2006.

(51) Int. Cl.
*A61K 31/59* (2006.01)
*C07C 401/00* (2006.01)

(52) U.S. Cl. .................... 514/167; 552/653
(58) Field of Classification Search .......... 552/653
See application file for complete search history.

(56) References Cited

U.S. PATENT DOCUMENTS

| | | | |
|---|---|---|---|
| 4,188,345 | A | 2/1980 | DeLuca et al. |
| 4,411,833 | A | 10/1983 | DeLuca et al. |
| 4,666,634 | A | 5/1987 | Miyamoto et al. |

(Continued)

FOREIGN PATENT DOCUMENTS

WO    WO 02/058707    8/2002

(Continued)

OTHER PUBLICATIONS

Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).

(Continued)

*Primary Examiner*—Sabiha Qazi
(74) *Attorney, Agent, or Firm*—Andrus, Sceales, Starke & Sawall, LLP

(57) ABSTRACT

This invention discloses 1α-hydroxy-2-(3'-hydroxypropy-lidene)-19-nor-vitamin D compounds with a 1,1-dimethyl-propyl side chain, and pharmaceutical uses therefor. These compounds exhibit pronounced activity in arresting the proliferation of undifferentiated cells and inducing their differentiation to the monocyte thus evidencing use as an anticancer agent and for the treatment of skin diseases such as psoriasis as well as skin conditions such as wrinkles, slack skin, dry skin and insufficient sebum secretion. These compounds also have little, if any, calcemic activity and therefore may be used to treat autoimmune disorders or inflammatory diseases in humans as well as renal osteodystrophy. These compounds may also be used for the treatment or prevention of obesity.

86 Claims, 5 Drawing Sheets

U.S. PATENT DOCUMENTS

| | | | |
|---|---|---|---|
| 4,970,203 | A | 11/1990 | DeLuca et al. |
| 5,086,191 | A | 2/1992 | DeLuca et al. |
| 5,446,035 | A | 8/1995 | Neef et al. |
| 5,536,713 | A | 7/1996 | DeLuca et al. |
| 5,585,369 | A | 12/1996 | DeLuca et al. |
| 5,843,928 | A | 12/1998 | DeLuca et al. |
| 5,880,114 | A | 3/1999 | DeLuca et al. |
| 5,936,133 | A | 8/1999 | DeLuca et al. |
| 5,945,410 | A | 8/1999 | DeLuca et al. |
| 6,127,559 | A | 10/2000 | DeLuca et al. |
| 6,277,837 | B1 | 8/2001 | DeLuca et al. |
| 6,291,444 | B1 | 9/2001 | DeLuca et al. |
| 6,306,844 | B1 | 10/2001 | DeLuca et al. |
| 6,382,071 | B1 | 5/2002 | Bertani et al. |
| 6,537,981 | B2 | 3/2003 | DeLuca et al. |
| 6,548,489 | B2 * | 4/2003 | Takenouchi et al. ......... 514/167 |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 6,844,330 | B2 | 1/2005 | DeLuca et al. |
| 6,844,331 | B2 | 1/2005 | DeLuca et al. |
| 6,844,332 | B2 | 1/2005 | DeLuca et al. |
| 6,844,457 | B2 | 1/2005 | DeLuca et al. |
| 6,846,811 | B2 | 1/2005 | DeLuca et al. |
| 7,053,075 | B2 | 5/2006 | DeLuca et al. |
| 2003/0158157 | A1 | 8/2003 | DeLuca et al. |
| 2004/0229851 | A1 | 11/2004 | DeLuca et al. |
| 2005/0119242 | A1 | 6/2005 | DeLuca et al. |
| 2006/0166949 | A1 * | 7/2006 | Binderup et al. ............ 514/167 |
| 2007/0191316 | A1 | 8/2007 | DeLuca et al. |
| 2007/0191317 | A1 | 8/2007 | DeLuca et al. |

FOREIGN PATENT DOCUMENTS

| | | |
|---|---|---|
| WO | WO 2004/092118 | 10/2004 |

OTHER PUBLICATIONS

Collins et al, "Normal Functional Characteristics of Cultured Human Promyelocytic Leukemia Cells (HL-60) After Inducation of Differentiation by Dimethylsulfoxide," The Journal of Experimental Medicine, vol. 149, pp. 969-974, (1979).

Corey et al, "Computer-Assisted Synthetic Analysis. A Rapid Computer Method for the Semiquantitative Assignment of Conformation of Six-Membered Ring Systems. 1. Derivation of a Preliminary Conformational Description of the Six-Membered Ring," The Journal of Organic Chemistry, vol. 45, No. 5, pp. 757-764, (1980).

Daniewski et al, "A Novel Silylcopper Catalyst for the Reductive Bromination of Hajos Dione. Improved Preparation of a CD Synthon for the Synthesis of Vitamin D," Journal of Organic Chemistry, vol. 66 No. 2, pp. 626-628, (2001).

Fall et al, "Vitamin D Heterocyclic Analogues. Part 1: A Stereoselective Route to CD Systems with Pyrazole Rings in their Side Chains," Tetrahedron Letters 43, pp. 1433-1436, (2002).

Glebocka et al, "New Derivative of 1α,25-Dihydroxy-19-Norvitamin $D_3$ with 3'-Alkoxypropylidene Moiety at C-2: Synthesis, Biological Activity and Conformational Analysis," Journal of Steroid Biochemistry & Molecular Biology, vols. 89-90, pp. 25-30, (2004).

Granja et al, "Studies on the Opening of Dioxanone and Acetal Templates and Application to the Synthesis of 1α,25-Dihydroxyvitamin $D_2$," Journal of Organic Chemistry, vol. 58, pp. 124-131, (1993).

Hanessian et al, "Total Synthesis of (—)-Reserpine Using the Chiron Approach," Journal of Organic Chemistry, vol. 62, pp. 465-473, (1997).

Inhoffen et al, "Studies in the Vitamin D Series, XXI: Hydrindane Compounds from Vitamin $D_3$," Chemische Berichte, vol. 90, pp. 664-673, (1957).

Lythgoe et al, "Calciferol and its Relatives. Part22. A Direct Total Synthesis of Vitamin $D_2$ and Vitamin $D_3$," J. Chem. Soc. Perkin Trans. 1, p. 590, (1978).

Lythgoe, "Synthetic Approaches to Vitamin D and its Relatives," Chem. Soc. Rev. 9, p. 449, (1983).

Mincione et al, "Improved Conversion of Vitamin $D_2$ into the Windaus Ketone and its Regioselective Hydroxylation via Organoboranes at $C_{26}$," Synthetic Communications, vol. 19 Nos. 5-6, pp. 723-735, (1989).

Miyamoto et al, "Synthetic Studies of Vitamin D Analogues. XIV. Synthesis and Calcium Regulating Activity of Vitamin $D_3$ Analogues Bearing a Hydroxyalkoxy Group at the 2β-Position," Chem. Pharm. Bull., vol. 41 No. 6, pp. 1111-1113, (1993).

Nishii et al, "The Development of Vitamin $D_3$ Analogues for the Treatment of Osteoporosis," Osteoporosis Int., Suppl. 1, pp. S190-S193, (1993).

Okamura et al, "Vitamin D: Concerning the Relationship Between Molecular Topology and Biological Function," Proc. Nat. Acad. Sci. U.S.A., vol. 71 No. 10, pp. 4194-4197 (1974).

Okano et al, "Regulatory Activities of 2β-(3-Hydroxypropoxy)-1α,25-Dihydroxy-Vitamin $D_3$, a Novel Synthetic Vitamin $D_3$ Derivative, on Calcium Metabolism," Biochemical and Biophysical Research Communications, vol. 163 No. 3, pp. 1444-1449, (1989).

Ono et al, "Efficient Synthesis of 2-Modified 1α,25-Dihydroxy-19-norvitamin $D_3$ with Julia Olefination: High Potency in Induction of Differentiation on HL-60 Cells," Journal of Organic Chemistry, vol. 68, pp. 7407-7415, (2003).

Ostrem et al, "24- and 26-homo-1,25-dihydroxyvitamin $D_3$: Preferential activity in inducing differentiation of human leukemia cells HL-60 in vitro," Proc. Natl. Acad. Sci. USA, vol. 84, pp. 2610-2614, (1987).

Perlman et al, "1α,25-Dihydroxy-19-Nor-Vitamin $D_3$. A Novel Vitamin D-Related Compound with Potential Therapeutic Activity," Tetrahedron Letters, vol. 31 No. 13, pp. 1823-1824, (1990).

Perlman et al, "Novel Synthesis of 19-Nor-Vitamin D Compounds," Tetrahedron Letters, vol. 32 No. 52, pp. 7663-7666, (1991).

Peterson et al, "Studies of the Ketone Obtained from the Ozonolysis of Vitamin D. Molecular Mechanics Calculations for It and Related Hydrindanones," Journal of Organic Chemistry, vol. 51 No. 11, pp. 1948-1954 (1986).

Plum et al, "Biologically Active Noncalcemic Analogs of 1α,25-Dihydroxyvitamin D with an Abbreviated Side Chain Containing No Hydroxyl," PNAS, vol. 101 No. 18, pp. 6900-6904, (2004).

Posner et al, "Stereocontrolled Total Synthesis of Calcitriol Derivatives: 1,25-Dihydroxy-2-(4'-hydroxybutyl)vitamin $D_3$ Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin $D_3$. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

Rochel et al, "The Crystal Structure of the Nuclear Receptor for Vitamin D Bound to Its Natural Ligand," Molecular Cell, vol. 5, pp. 173-179, (2000).

Sardina et al, "Studies on the Synthesis of Side-Chain Hydroxylated Metabolites of Vitamin D. 2. Stereocontrolled Synthesis of 25-Hydroxyvitamin $D_2$," J. Org. Chem., 51, pp. 1264-1269, (1986).

Sicinski et al, "New 1α,25-Dihydroxy-19-Norvitamin $D_3$ Compounds of High Biological Activity: Synthesis and Biological Evaluation of 2-Hydroxymethyl, 2-Methyl, and 2-Methylene Analogues," Journal of Medical Chemistry, 41, pp. 4662-4674, (1998).

Sicinski et al, "New Highly Calcemic 1α,25-Dihydroxy-19-Norvitamin $D_3$ Compounds with Modified Side Chain: 26,27-Dihomo- and 26,27-Dimethylene Analogs in 20S-Series," Steroids, vol. 67, pp. 247-256, (2002).

Sicinski et al, "2-Ethyl and 2-Ethylidene Analogues of 1α,25-Dihydroxy-19-Norvitamin $D_3$: Synthesis, Conformational Analysis, Biological Activities, and Docking to the Modeled rVDR Ligand Binding Domain," Journal of Medical Chemistry, vol. 45, pp. 3366-3380, (2002).

Tocchini-Valentini et al, "Crystal Structures of the Vitamin D Receptor Complexed to Superagonist 20-epi Ligands," Proc. Natl. Acad. Sci. USA, vol. 98 No. 10, pp. 5491-5496, (2001).

Toh et al, "Studies on a Convergent Route to Side-Chain Analogues of Vitamin D: 25-Hydroxy-23-Oxavitamin $D_3$," J. Org. Chem., 48, 1414, (1983).

Windaus et al, "The Constitution of Vitamin $D_2$ Part II," Annalen der Chemie, 524, pp. 295-299, (1936).

Yoshida et al, "Efficient and Convergent Coupling Route for the Short-step Synthesis of Enantiopure 2α- and 2β-Alkylated 1α,25-Dihydroxy-19-norvitamin $D_3$ Analogues," Synlett, No. 8, pp. 1175-1179, (2003).

* cited by examiner

1α-HYDROXY-2-(3'-HYDROXYPROPYL-IDENE)-19-NOR-VITAMIN D COMPOUNDS WITH A 1,1-DIMETHYLPROPYL SIDE CHAIN

CROSS REFERENCE TO RELATED APPLICATIONS

This application claims priority to and the benefit of U.S. Provisional Application No. 60/791,487, filed Apr. 10, 2006.

BACKGROUND OF THE INVENTION

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

In 1990, a new class of vitamin D analogs was discovered, i.e. the so called 19-nor-vitamin D compounds, characterized by the replacement of the ring A exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, with very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Letters 31, 1823 (1990); Perlman et al., Tetrahedron Letters 32, 7663 (1991), and DeLuca et al., U.S. Pat. No. 5,086,191). A few years later, analogs of 1α,25-dihydroxy-19-norvitamin $D_3$ substituted at 2-position with hydroxy or alkoxy groups (DeLuca et al., U.S. Pat. No. 5,536,713) were synthesized. It has been established that they exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the transposition of the ring A exocyclic methylene group from carbon 10 (C-10) to carbon 2 (C-2), i.e. 2-methylene-19-nor-vitamin D compounds have been recently synthesized and tested (Sicinski et al., J. Med. Chem., 41, 4662 (1998); Sicinski et al., Steroids 67, 247 (2002); DeLuca et al., U.S. Pat. Nos. 5,843,928, 5,936,133 and 6,382,071). Molecular mechanics studies, performed on these analogs, showed that a change of ring-A conformation can be expected resulting in the "flattening" of the cyclohexanediol ring. From molecular mechanics calculations and NMR studies their A-ring conformational equilibrium was established to be ca. 6:4 in favor of the conformer that has an equatorial 1α-OH. Introduction of the 2-methylene group into 19-nor-vitamin D carbon skeleton changes the character of its (1α- and 3β-) A-ring hydroxyls; they are both now in the allylic positions, similar, to the 1α-hydroxyl group (crucial for biological activity) in the molecule of the natural hormone, 1 α,25-$(OH)_2D_3$. It was found that 1α,25-dihydroxy-2-methylene-19-norvitamin D analogs are characterized by significant biological potency, enhanced dramatically in compounds with an "unnatural" (20S)-configuration.

Recently, 2-ethylidene analogs of 1α,25-dihydroxy-19-norvitamin $D_3$ have been synthesized. It turned out that such modification of the ring A resulted in significant biological potency for the compounds, especially enhanced in the E-geometrical isomers, Sicinski et al., J. Med. Chem., 45, 3366 (2002). Interestingly, it has been established that E-isomers have A-ring conformational equilibrium considerably shifted to one particular chair form, that possessing 1α-hydroxyl in an equatorial orientation.

Very recently, derivatives of 1α,25-dihydroxy-19-norvitamin $D_3$ with 3'-hydroxypropylidene moiety at C-2 (DeLuca et. al, US Patent Application 20040229851) have been synthesized. Interestingly, their in vivo calcemic activity significantly exceeded that of 1α,25-$(OH)_2D_3$, especially in stimulating intestinal calcium transport. Molecular modeling studies of these analogs indicated that the presence of an oxygen function, located at the terminus of the propylidene fragment, could introduce additional interaction with the vitamin D receptor. In fact, the affinity of the synthesized compounds to VDR was increased and approached that of the natural hormone. Taking into account the recent findings on 2-methylene-1α-hydroxy-19-norvitamin D analogs with truncated side chain, Plum et al., PNAS, 101, 6900 (2004), indicating that these compounds effectively suppress parathyroid hormone levels, it was decided to further explore such modification of the vitamin D molecule.

As a continuation of the search for biologically active 2-alkylidene-19-norvitamin D compounds, analogs which are characterized by the presence of a 3'-hydroxypropylidene moiety at C-2 and a branched (1,1-dimethylpropyl) alkyl side chain containing no hydroxyl group have now been synthesized and tested.

SUMMARY OF THE INVENTION

The present invention is directed toward 1α-hydroxy-2-(3'-hydroxypropylidene)-19-nor vitamin D compounds having a 1,1-dimethylpropyl side chain, their biological activity, and various pharmaceutical uses for these compounds.

A class of 1α-hydroxylated vitamin D compounds not known heretofore are the vitamin D isomers having the A-ring exocyclic methylene moiety at C-10 removed and possessing an additional fragment, being a substituted hydroxypropylidene group, attached to carbon-2. These compounds are also substituted at C-17 with a 1,1-dimethylpropyl group.

Structurally these novel analogs are characterized by the general formula I shown below:

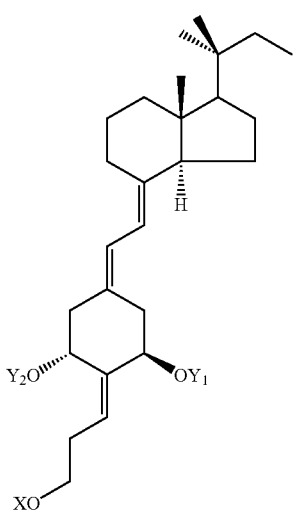

where $Y_1$ and $Y_2$, which may be the same or different, are each selected from the group consisting of hydrogen and a hydroxy-protecting group, and where X may be selected from the group consisting of an alkyl, a hydrogen, a hydroxy-protecting group, a hydroxyalkyl, an alkoxyalkyl and an aryloxyalkyl. Preferred are the E-geometrical isomers of 2-propylidene unit (possessing trans-orientation of substituents of terminal carbon atoms in the A-ring 1,4-dimethylenecyclohexane fragment).

The above compounds I, exhibit a desired, and highly advantageous, pattern of biological activity. These compounds are characterized by relatively high binding to vitamin D receptors, but very low intestinal calcium transport activity, as compared to that of 1α,25-dihydroxyvitamin $D_3$, and have very low ability to mobilize calcium from bone, as compared to 1α,25-dihydroxyvitamin $D_3$. Hence, these compounds can be characterized as having little, if any, calcemic activity. It is undesirable to raise serum calcium to supraphysiologic levels when suppressing the preproparathyroid hormone gene (Darwish & DeLuca, Arch. Biochem. Biophys. 365, 123-130, 1999) and parathyroid gland proliferation. These analogs having little or no calcemic activity while very active on differentiation are expected to be useful as a therapy for suppression of secondary hyperparathyroidism of renal osteodystrophy.

The compounds I of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I are also characterized by relatively high cell differentiation activity. Thus, these compounds also provide a therapeutic agent for the treatment of psoriasis, or as an anti-cancer agent, especially against leukemia, colon cancer, breast cancer, skin cancer, lung cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat or prevent the above-noted diseases and disorders in an amount from about 0.01 μg/gm to about 10 mg/gm of the composition, preferably from about 0.1 μg/gm to about 1 mg/gm of the composition, and may be administered topically, transdermally, orally, rectally, nasally, sublingually, or parenterally in dosages of from about 0.01 μg/day to about 10 mg/day, preferably from about 0.1 μg/day to about 1 mg/day.

BRIEF DESCRIPTION OF THE DRAWINGS

FIG. 1 is a graph illustrating the relative activity of 20DC and 1,25(OH)$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of 20DC and 1,25(OH)$_2$D$_3$;

FIG. 3 is a graph illustrating the in vitro transcription activity of 1,25(OH)$_2$D$_3$ as compared to 20DC;

FIG. 4 is a bar graph illustrating the bone calcium mobilization activity of 1,25(OH)$_2$D$_3$ as compared to 20DC; and FIG. 5 is a bar graph illustrating the intestinal calcium transport activity of 1,25(OH)$_2$D$_3$ as compared to 20DC.

DETAILED DESCRIPTION OF THE INVENTION

Figure 1:
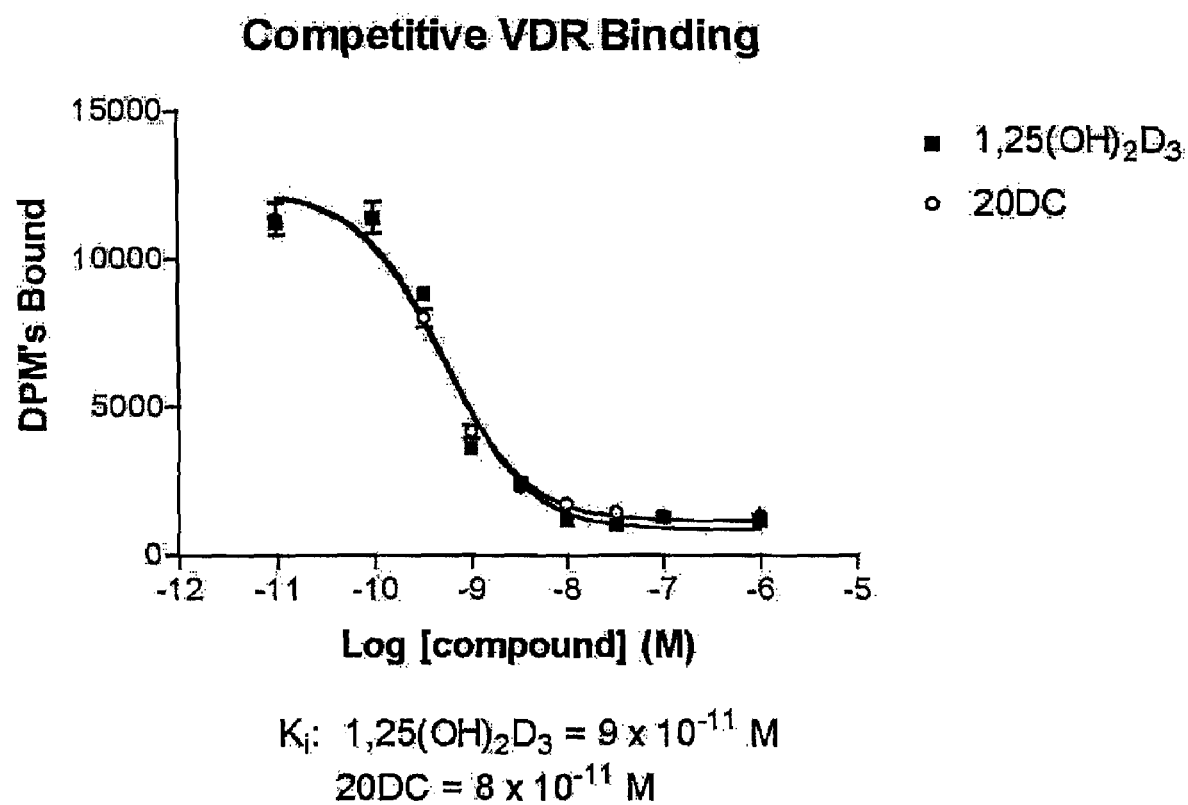
FIGS. 1-5 illustrate various biological activities of 1α-hydroxy-2-[3'-hydroxypropylidene]-20-methyl-19,24,25,26,27-pentanorvitamin $D_3$ (E-isomer) analog 11, hereinafter referred to as "20DC" as compared to the native hormone 1α,25-dihydroxyvitamin $D_3$, hereinafter "1,25(OH)$_2$D$_3$."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. "Aryloxy" refers to any aryl compound which is attached by oxygen, i.e. a group represented by "aryl-O—". Aryloxyalkyl refers to a group represented by "aryl-O-alkyl-".

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$-where k is an integer.

The preparation of 1α-hydroxy-19-nor-vitamin D compounds, with the substituted propylidene moiety at C-2, of the basic structure I can be accomplished by a common general method, i.e. the condensation of a bicyclic Windaus-Grundmann type ketone II with the allylic phosphine oxide III:

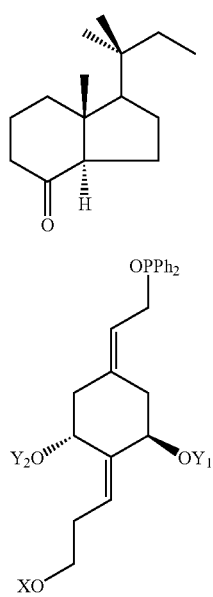

In the structure III, groups $Y_1$, $Y_2$ and X represent groups defined above; being preferably hydroxy-protecting groups. The process shown above represents an application of the convergent synthesis concept, which has been applied effectively for the preparation of vitamin D compounds (e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713).

The required phosphine oxides of general structure III are known, or can be prepared from commercial (1R,3R,4S,5R)-(−)-quinic acid as described previously [Glebocka et al., J. Steroid Biochem. Mol. Biol. 89-90, 25 (2004), DeLuca et. al, US Patent Application 20040229851].

For the preparation of the required hydrindanone of the structure II, a new synthetic route has been developed starting from the known [Fall et al., Tetrahedron Lett., 43, 1433 (2002); Granja et al., J. Org. Chem., 58, 124 (1993)] 22-aldehyde 1. A process involving transformation of the starting benzoyloxy aldehyde 1 into the desired C,D-ring synthon 8, and its subsequent coupling with the phosphine oxide 9, is summarized by the SCHEME I. Thus, the aldehyde 1 was transformed into the mixture of isomeric E- and Z-oximes which on heating with acetic anhydride formed the expected nitrile 2. The nitrile was treated with LDA and the resulted carbanion alkylated by addition of ethyl bromide. The subsequent steps of the synthesis comprise the alkaline hydrolysis of 8β-benzoyloxy group in the obtained nitrile 3 producing the corresponding hydroxy nitrile 4. This process is desired in view of the following chemical transformation, i.e. DIBALH reduction of the C-20 cyano group leading to the hydroxy aldehyde 5. Direct DIBALH reduction of benzoyloxy nitrile 3 does not provide 5 in satisfactory yield whereas two-step procedure turns out to be significantly more efficient. Then, the formyl substituent at C-20 was converted into methyl group by the following two-step procedure: formation of p-tosylhydrazone 6 and its reduction with sodium cyanoborohydride. The obtained 8β-alcohol 7 was subsequently oxidized with tetrapropylammonium perruthenate to the hydrindanone 8. Wittig-Horner coupling of this Grundmann ketone with lithium phosphinoxy carbanion generated from the phosphine oxide 9 and phenyllithium gave the expected protected vitamin compound 10. This, after deprotection with tetrabutylammonium fluoride afforded 1α-hydroxy-2-[3'-hydroxypropylidene]-20-methyl-19,24,25,26,27-pentanorvitamin $D_3$ (11). In the experimental part this synthesis is described as EXAMPLE I.

It should be noted that other 1α-hydroxy-2-[3'-hydroxypropylidene]-19-nor-vitamin D analogs with the shortened alkyl side chains may be synthesized by the methods disclosed herein.

This invention is described by the following illustrative examples. In these examples specific products identified by Arabic numerals (e.g. 1, 2, 3, etc) refer to the specific structures so identified in the preceding description and in the SCHEME I.

EXAMPLES

Chemistry. Melting points (uncorrected) were determined on a Thomas-Hoover capillary melting-point apparatus. Ultraviolet (UV) absorption spectra were recorded with a Perkin-Elmer Lambda 3B UV-VIS spectrophotometer in ethanol. $^1$H nuclear magnetic resonance (NMR) spectra were recorded at 400 and 500 MHz with a Bruker Instruments DMX-400 and DMX-500 Avance console spectrometers in deuteriochloroform. Chemical shifts (δ) are reported downfield from internal $Me_4Si$ (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example I

Preparation of 1α-hydroxy-2-[3'-hydroxypropylidene]-20-methyl-19,24,25,26,27-pentanorvitamin D$_3$ (11)

Referring first to SCHEME I the starting bicyclic aldehyde 1 was obtained according to the described procedure, Fall et al., Tetrahedron Lett., 43, 1433 (2002).

Conversion of the aldehyde 1 into 22-nitrile 2

Benzoic acid-(1R,3aR,4S,7aR)-1-((R)-cyano-methyl-methyl)-7a-methyl-octahydro-inden-4-yl ester (2). To a solution of a benzoyloxy aldehyde 1 (284 mg, 0.90 mmol) in anhydrous pyridine (5 mL) was added NH$_2$OH×HCl (210 mg) and the mixture was stirred at room temperature for 20 h. Then it was poured into water and extracted with ethyl acetate. The combined organic phases were separated, washed with saturated NaHCO$_3$ solution, water, and saturated CuSO$_4$ solution, dried (MgSO$_4$) and evaporated. The oily residue was purified by column chromatography on silica gel. Elution with hexane/ethyl acetate (9:1) gave pure, less polar E-oxime (167 mg) and more polar Z-oxime (105 mg, total yield 89%).

E-oxime: $^1$H NMR (400 MHz, CDCl$_3$) δ 1.09 (3H, d, J=6.7 Hz, 18-H$_3$), 1.14 (3H, s, 21-H$_3$), 2.40 (1H, m, 20-H), 5.42 (1H, narr m, 8α-H), 7.27 (1H, d, J=8.0 Hz, 22-H), 7.45 (2H, t, J~7 Hz, Ar—H), 7.56 (1H, t, J=7.4 Hz, Ar—H), 8.04 (2H, d, J=7.4 Hz, Ar—H).

Z-oxime: $^1$H NMR (400 MHz, CDCl$_3$) δ 1.09 (3H, d, J=6.7 Hz, 18-H$_3$), 1.13 (3H, s, 21-H$_3$), 3.28 (1H, m, 20-H), 5.42 (1H, narr m, 8α-H), 6.25 (1H, d, J=8.1 Hz, 22-H), 7.45 (2H, t, J~7 Hz, Ar—H), 7.56 (1H, t, J=7.3 Hz, Ar—H), 8.04 (2H, d, J=7.3 Hz, Ar—H).

The solution of the oximes (both isomers, 248 mg, 0.75 mmol) in acetic anhydride (8 mL) was refluxed for 1.5 h. The reaction mixture was cooled, poured carefully on ice and extracted with toluene. Extracts were combined, washed with water, NaHCO$_3$ and brine, dried (MgSO$_4$) and evaporated. The residue was applied on a silica Sep-Pak (5 g). Elution with hexane/ethyl acetate (95:5) gave pure semicrystalline nitrile 2 (212 mg, 91%). 2: [α]$^{24}_D$+81.5° (c 0.9 CHCl$_3$); $^1$H NMR (400 MHz, CDCl$_3$) δ 1.124 (3H, s, 18-H$_3$), 1.373 (3H, d, J=7.1 Hz, 21-H$_3$), 1.90 (1H, br d, J=12.8 Hz, 9β-H), 2.68 (1H, pentet, J=7.0 Hz, 20-H), 5.43 (1H, narr m, 8α-H), 7.45 (2H, t, J=7.5 Hz, Ar—H), 7.57 (1H, t, J=7.5 Hz, Ar—H), 8.03 (2H, d, J=7.4 Hz, Ar—H); HRMS (ESI) exact mass calcd for C$_{13}$H$_{20}$ON (M$^+$-C$_6$H$_5$CO) 206.1545, measured 206.1539.

Alkylation of the nitrile 2 with ethyl bromide

Benzoic acid-(1S,3aR,4S,7aR)-1-((S)-1-cyano-1-methylpropyl)-7a-methyl-octahydro-inden-4-yl ester (3). n-BuLi (1.6 M in hexanes, 1.0 mL, 1.6 mmol) was added at 0° C. to the flask containing diisopropylamine (262 μL, 1.54 mmol) and THF (2 mL). The solution was stirred at 0° C. for 20 min., cooled to −78° C. and siphoned to the solution of 2 (430 mg, 1.31 mmol) in THF (1.5 mL). The resulted yellow mixture was stirred for 30 min, then HMPA (600 μL) was added and stirring was continued for another 15 min. Then CH$_3$CH$_2$Br (310 μL, 4.08 mmol) was added, and the solution was stirred at −78° C. for 40 min. Saturated NH$_4$Cl was added and the mixture was extracted with ethyl acetate. The combined organic phases were washed with water, dried (MgSO$_4$) and evaporated. The residue was applied on a silica column. Elution with hexane/ethyl acetate (95:5) resulted in pure compound 3 (280 mg, 60%; 80% based on recovered substrate). Further elution with hexane/ethyl acetate (95:5) gave unreacted 2 (107 mg). 3: [α]$^{24}_D$+117.5° (c 0.2 CHCl$_3$); $^1$H NMR (400 MHz, CDCl$_3$) δ 1.023 (3H, t, J=7.4 Hz, 23-H$_3$), 1.337 (3H, s, 18-H$_3$), 1.397 (3H, s, 21-H$_3$), 2.14 (1H, br d, J=12.9 Hz, 9β-H), 5.40 (1H, narr m, 8α-H), 7.45 (2H, t, J=7.4 Hz, Ar), 7.57 (1H, t, J=7.4 Hz, Ar), 8.05 (2H, d, J=7.4 Hz, Ar).

Hydrolysis of the Benzoate 3

(S)-2-((1S,3aR,4S,7aR)-4-Hydroxy-7a-methyl-octahydro-inden-1-yl)-2-methyl-butylonitrile (4). A solution of the benzoyloxy nitrile 3 (270 mg, 0.76 mmol) in 10% KOH in MeOH (12 mL) was heated at 50° C. for 18 h, poured into water and extracted with ethyl acetate. Organic phase was washed with NaHCO$_3$, water, dried (MgSO$_4$) and evaporated. The oily residue was purified by a silica Sep-Pak (2 g). Elution with hexane/ethyl acetate (8:2) gave pure hydroxyl nitrile 4 (179 mg, 99%). 4: [α]$^{24}_D$+26.50 (c 0.33 CHCl$_3$); $^1$H NMR (400 MHz, CDCl$_3$) δ 1.004 (3H, t, J=7.3 Hz, 23-H$_3$), 1.349 (3H, s, 21-H$_3$), 1.240 (s, 18-H$_3$), 4.10 (1H, narr m, 8α-H).

Reduction of the Nitrile 4 with DIBALH (S)-2-((1S,3aR,4S,7aR)-4-Hydroxy-7a-methyl-octahydro-inden-1-yl)-2-methyl-butyraldehyde (5). To the solution of nitrile 4 (172 mg, 0.773 mmol) in anhydrous methylene chloride (3.3 mL) a solution of DIBALH (1.5 M in toluene, 1.66 mL, 2.3 mmol) was slowly added at −60° C. The solution was stirred for 1 h 30 min., then it was allowed to warm up to −30° C. during 1 h and the stirring was continued for 50 min. The mixture was carefully poured into 5% HCL and extracted with ethyl acetate. The combined organic layers were washed with NaHCO$_3$ and brine, dried (MgSO$_4$) and evaporated. The remaining residue was purified by a silica Sep-Pak (2 g). Elution with hexane/ethyl acetate (8:2) gave pure hydroxy aldehyde 5 (57 mg, 33%). 5: [α]$^{24}_D$+5° (c 0.25 CHCl$_3$); $^1$H NMR (400 MHz, CDCl$_3$) δ 0.781 (3H, t, J=7.3 Hz, 23-H$_3$), 0.965 (3H, s, 21-H$_3$), 1.105 (3H, s, 18-H$_3$), 2.02 (1H, br d, J=14.2 Hz, 9β-H), 4.09 (1H, narr m, 8α-H), 9.72 (1H, s, CHO); HRMS (ESI) exact mass calcd for C$_{14}$H$_{26}$O (M$^+$+Na) 261.1831, measured 261.1847.

Conversion of the hydroxy aldehyde 5 into a hydrindanol 7

(1R,3aR,4S,7aR)-1-(1,1-Dimethyl-propyl)-7a-methyl-octahydro-inden-4-ol (7). A solution of the aldehyde 5 (10 mg, 0.42 μmol) and p-toluenesulfonyl hydrazide (31 mg, 0.168 mmol) in a dry methanol (0.5 mL) was stirred with molecular sieves 4 Å at 55° C. for 19 h. Then it was cooled, poured into water and extracted with toluene. The combined organic phases were washed with water, dried (MgSO$_4$), evaporated and applied on a silica Sep-Pak (2 g). Elution with hexane/ethyl acetate (85:15) gave tosylhydrazone 6 (ca. 12 mg, ca. 67%) slightly contaminated with TsNHNH$_2$. This crude tosylhydrazone was dissolved in DMF (0.15 mL) and p-TsOH (2 mg, evaporated twice with benzene) was added followed by NaBH$_3$CN (8 mg, 0.126 mmol). The mixture was stirred at 100° C. for 19 h, then it was cooled, poured into water and extracted with hexane and ethyl acetate. The combined organic phases were washed with water, dried (MgSO$_4$) and evaporated. The remaining oily residue was applied on a silica Sep-Pak (2 g). Elution with hexane/ethyl acetate (98:2) gave a hydroxy compound 7 (4 mg, 65%). 7: [α]$^{24}_D$+3° (c 0.25 CHCl$_3$); $^1$H NMR (500 MHz, CDCl$_3$) δ 0.786 (3H, t, J=7.6 Hz, 23-H$_3$), 0.857 and 0.914 (3H and 3H, each s, 20-CH$_3$ and 21-H$_3$), 1.056 (3H, s, 18-H$_3$), 2.05 (1H, br d, J~10.5 Hz, 9-βH), 4.07 (1H, narr m, 8α-H).

Oxidation of 7 to a Hydrindanone 8

(1R,3aR,7aR)-1-(1,1-Dimethyl-propyl)-7a-methyl-octahydro-inden-4-one (8). The solution of NMO (7.2 mg) and molecular sieves 4 Å (41 mg) in methylene chloride (0.3 mL) was stirred at room temperature for 15 min., then the solution of 7 (6 mg, 27 μmol) in methylene chloride (0.15 mL) was added followed by TPAP (0.8 mg). The resulted dark mixture was stirred for 30 min., diluted with methylene chloride and applied on a silica Sep-Pak (2 g). Elution with hexane/ethyl acetate (96:4) gave a pure ketone 8 (3.5 mg, 59%). 8: [α]$^{24}_D$−

43° (c 0.18 CHCl$_3$); $^1$H NMR (500 MHz, CDCl$_3$) δ 0.721 (3H, s, 18-H$_3$), 0.825 (3H, t, J=7.3 Hz, 23-H$_3$), 0.872 and 0.945 (3H and 3H, each s, 20-CH$_3$ and 21-H$_3$), 2.41 (1H, dd, J=11.0, 7.5 Hz, 14α-H).

Wittig-Horner Coupling of the Ketone 8 with the Phosphine Oxide 9

1α-[(tert-Butyldimethylsilyl)oxy]-2-[3'-[((tert-butyldimethylsilyl)oxy)propylidene]-20-methyl-19,24,25,26,27-pentanorvitamin D$_3$ tert-Butyldimethylsilyl Ether (E-isomer, 10). To a solution of phosphine oxide 9 (35 mg, 48 μmol) in anhydrous THF (0.40 mL) at −78° C. was slowly added phenyllithium (1.8 M in butyl ether, 32 μL, 57 μmol) under argon with stirring. The solution turned deep orange. The mixture was stirred at −78° C. for 20 min and a precooled (−78° C.) solution of the ketone 8 (1.7 mg, 7.6 μmol) in anhydrous THF (0.08 mL) was slowly added. The mixture was stirred under argon at −78° C. for 2 h and at 6° C. for 16 h. Ethyl acetate and water were added, and the organic phase was washed with brine, dried (MgSO$_4$), and evaporated. The residue was dissolved in hexane, applied on a silica column, and eluted with hexane/ethyl acetate (99.5:0.5) to give silylated 19-norvitamin 10 (2.8 mg, 48%). The column was then washed with hexane/ethyl acetate (6:4) to recover the unreacted phosphine oxide 9 (30 mg). 10: $^1$H NMR (400 MHz, CDCl$_3$) δ 0.049, 0.054, 0.058, 0.063 and 0.069 (3H, 3H, 3H, 3H and 6H, each s, 6×SiCH$_3$), 0.634 (3H, s, 18-H$_3$), 0.816, 0.895 and 0.923 (each 9H, each s, 3×Si-t-Bu), 2.75 (1H, dm, J~13 Hz, 9β-H), 3.05 (1H, dd, J=12.6, 4.4 Hz, 10β-H), 3.61 (2H, m, CH$_2$—CH$_2$—O), 4.34 (1H, m, w/2=20 Hz, 1β-H), 4.80 (1H, narr m, 3α-H), 5.47 (1H, t, J=7.3 Hz, HC=C—CH$_2$), 5.86 and 6.11 (1H and 1H, each d, J=11.2 Hz, 7- and 6-H); HRMS (ESI) exact mass calcd for C$_{44}$H$_{84}$O$_3$Si$_3$Na (M$^+$+Na) 767.5626, measured 767.5644.

Hydrolysis of the silyl protecting groups in the 19-norvitamin D derivative 10

1α-Hydroxy-2-[3'-hydroxypropylidene]-20-methyl-19,24,25,26,27-pentanorvitamin D$_3$ (E-isomer, 11). To a solution of the protected vitamin 10 (2.7 mg, 3.6 μmol) in anhydrous THF (2 mL) was added tetrabutylammonium fluoride (1.0 M in THF, 166 μL, 166 μmol) and triethylamine (23 μL). The mixture was stirred under argon at room temperature for 18 h, poured into brine and extracted with ethyl acetate and diethyl ether. The combined organic extracts were washed with brine, dried (MgSO$_4$), and evaporated. The residue was purified by HPLC (9.4 mm×25 cm Zorbax-Sil column, 4 mL/min) using hexane/2-propanol (7:3) solvent system. Pure 19-norvitamin 11 (1.1 mg, 75%) was collected at R$_V$ 24.5 mL. In reversed-phase HPLC (9.4 mm×25 cm Eclipse XDB-C18 column, 3 mL/min) using methanol/water (95:5) solvent system vitamin 11 was collected at R$_V$ 27 mL. 11 (20DC): UV (in EtOH) λ$_{max}$ 243.0, 251.5, 261.5 nm; $^1$H NMR (400 MHz, CDCl$_3$) δ 0.632 (3H, s, 18-H$_3$), 0.860 and 0.923 (3H and 3H, each s, 20-CH$_3$ and 21-H$_3$), 0.872 (3H, t, J=7.3 Hz, 23-H$_3$), 2.46 (2H, narr m, 4α- and 4β-H), 2.35 and 2.54 (1H and 1H, each m,=CH—CH$_2$), 2.80 (1H, br d, J=12.6 Hz, 9β-H), 3.16 (1H, dd, J=13.0, 4.6 Hz, 10-H), 3.63 and 3.75 (1H and 1H, each m, CH$_2$—CH$_2$—O), 4.44 (1H, m, w/2=21 Hz, 1-H), 4.85 (1H, narr m, 3α-H), 5.66 (1H, t, J=7.7 Hz, HC=C—CH$_2$), 5.87 and 6.30 (1H and 1H, each d, J=11.1 Hz, 7- and 6-H); HRMS (ESI) exact mass calcd for C$_{26}$H$_{42}$O$_3$Na (M$^+$+Na) 425.3032, measured 425.3023.

SCHEME I

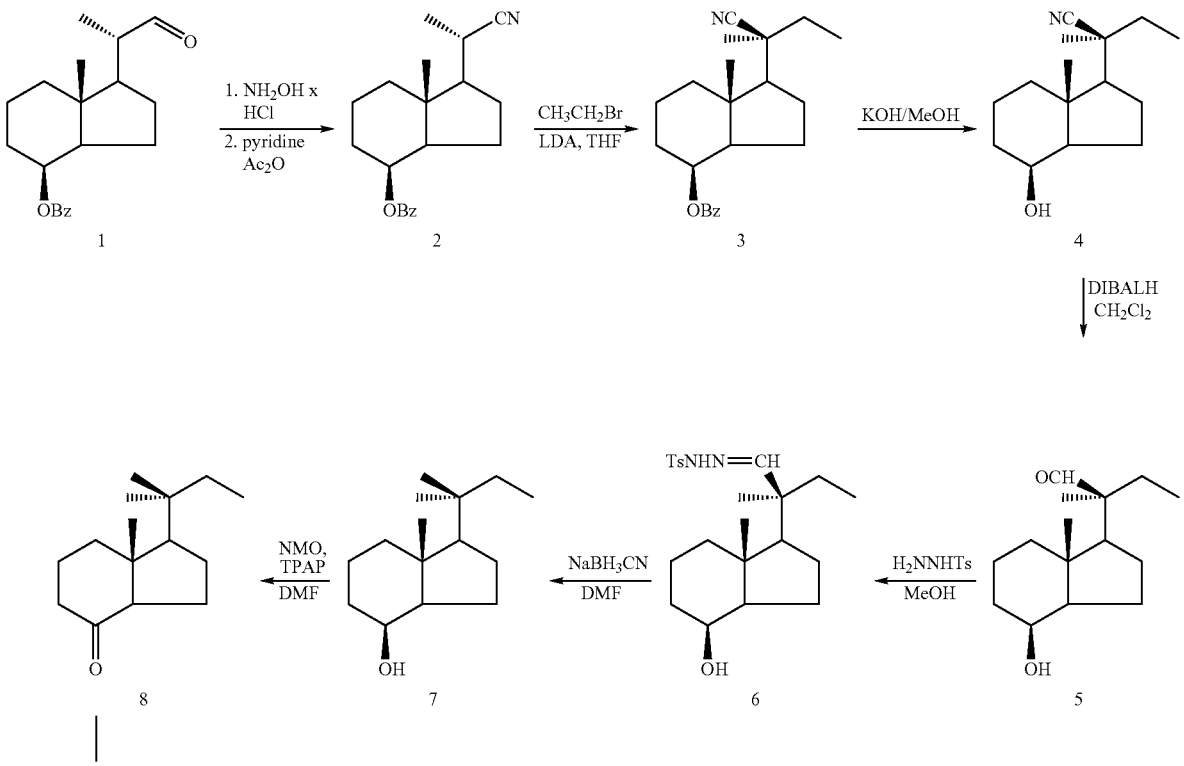

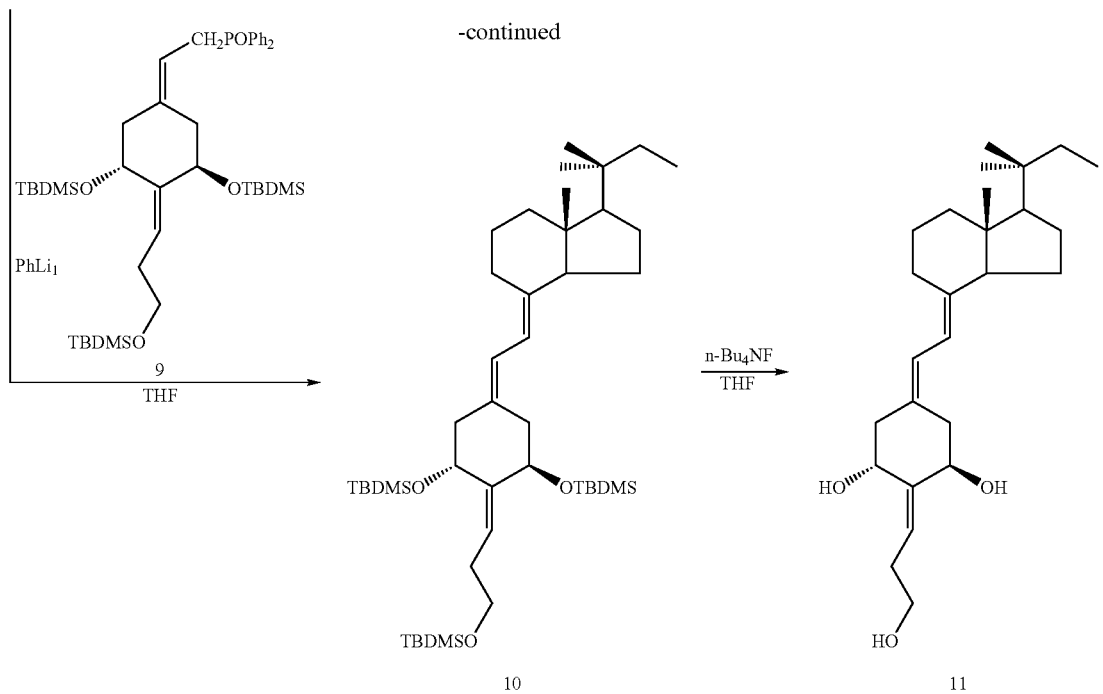

BIOLOGICAL ACTIVITY OF 1α-HYDROXY-2-[3'-HYDROXYPROPYLIDENE]-20-METHYL-19,24,25,26,27-PENTANORVITAMIN $D_3$ (E-ISOMER, 11)

The introduction of a 3'-hydroxypropylidene group to the 2-position, and the elimination of carbons 24, 25, 26 and 27 in the side chain of 1α-hydroxy-19-nor-vitamin $D_3$ had little effect on binding to the full length recombinant rat vitamin D receptor, as compared to 1α,25-dihydroxyvitamin $D_3$. The compound 20DC bound equally well to the receptor as compared to the standard 1,25-$(OH)_2D_3$ (FIG. 1). It might be expected from these results that compound 20DC would have equivalent biological activity. Surprisingly, however, compound 20DC is a highly selective analog with unique biological activity.

Figure 5:
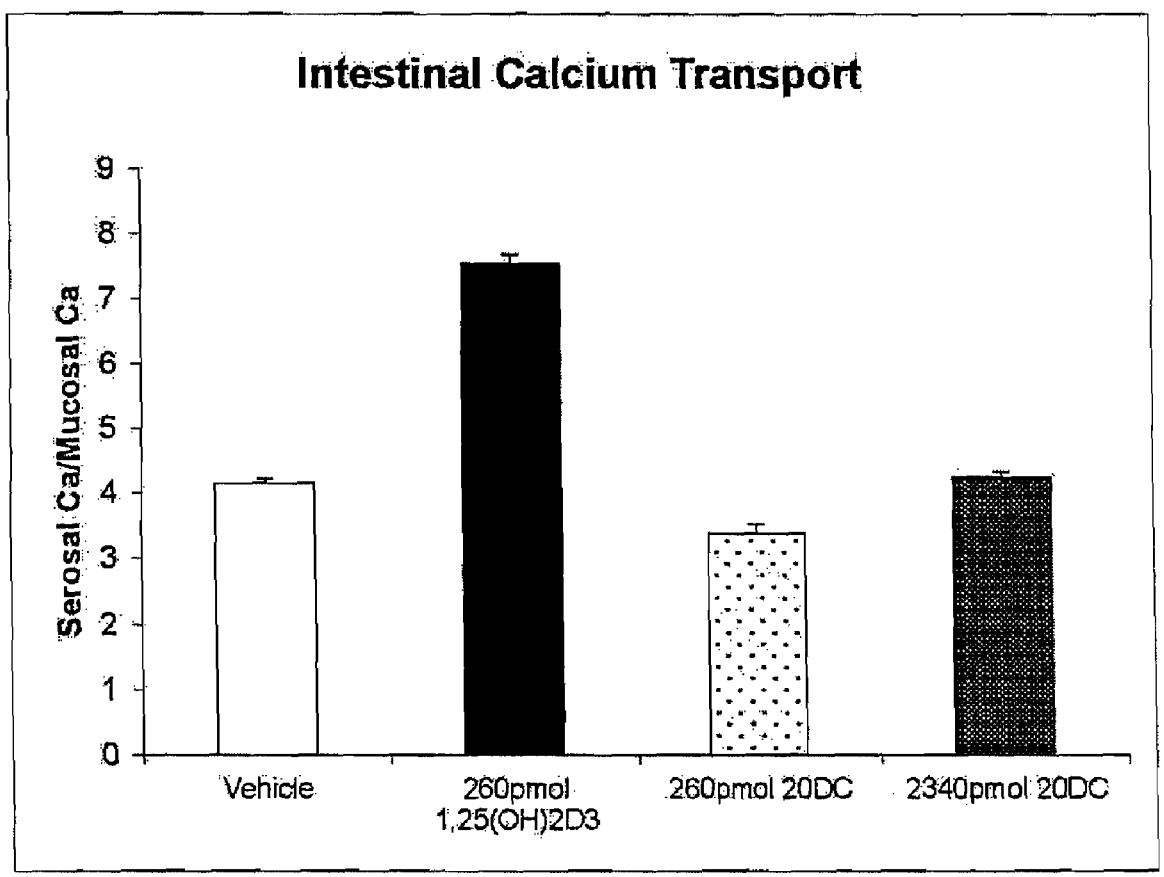

FIG. 5 shows that 20DC has very little activity as compared to that of 1,25-dihydroxyvitamin $D_3$ (1,25$(OH)_2D_3$), the natural hormone, in stimulating intestinal calcium transport.

Figure 4:
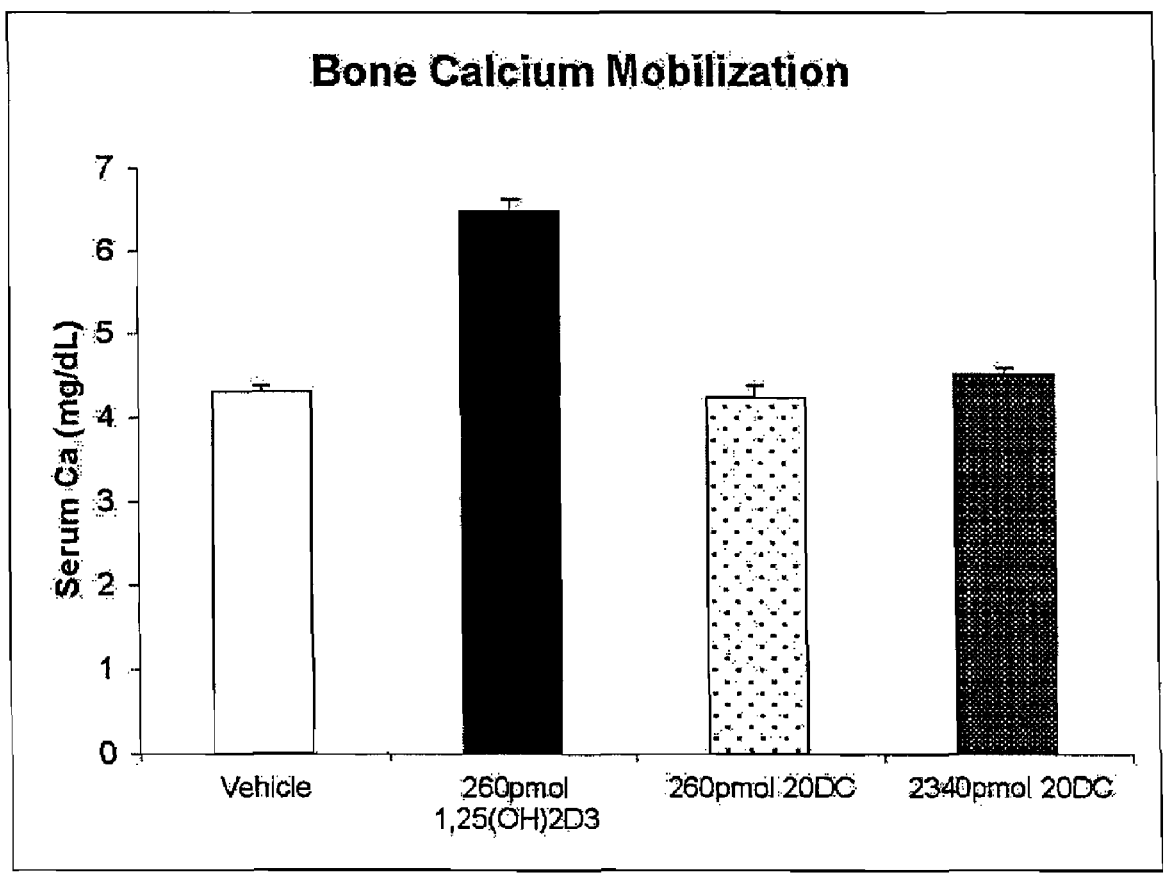

FIG. 4 demonstrates that 20DC has very little bone calcium mobilization activity, as compared to 1,25$(OH)_2D_3$.

FIGS. 4 and 5 thus illustrate that 20DC may be characterized as having little, if any, calcemic activity.

Figure 2:
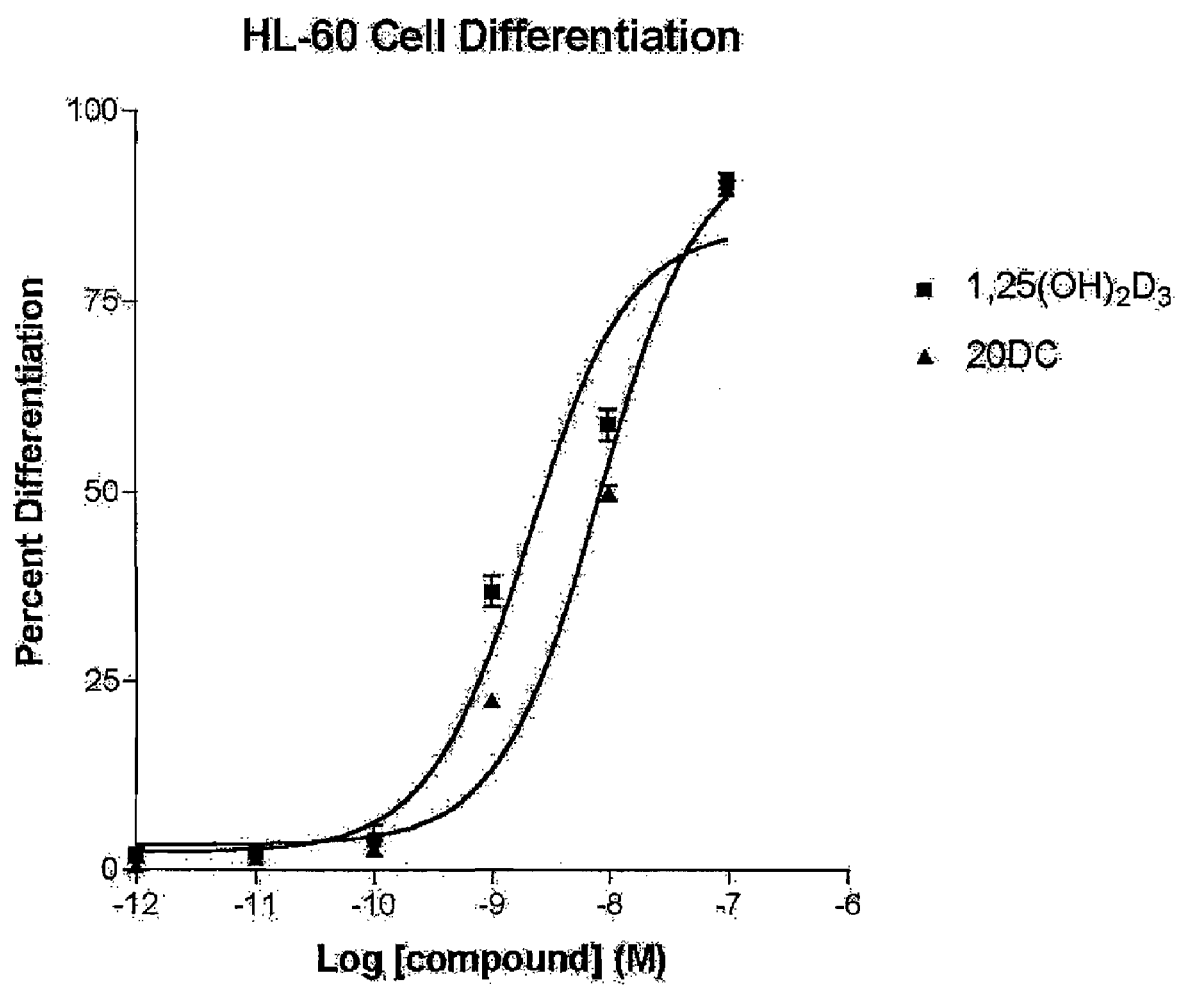

FIG. 2 illustrates that 20DC is about as potent as 1,25$(OH)_2D_3$ on HL-60 cell differentiation, making it an excellent candidate for the treatment of psoriasis and cancer, especially against leukemia, colon cancer, breast cancer, skin cancer, lung cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
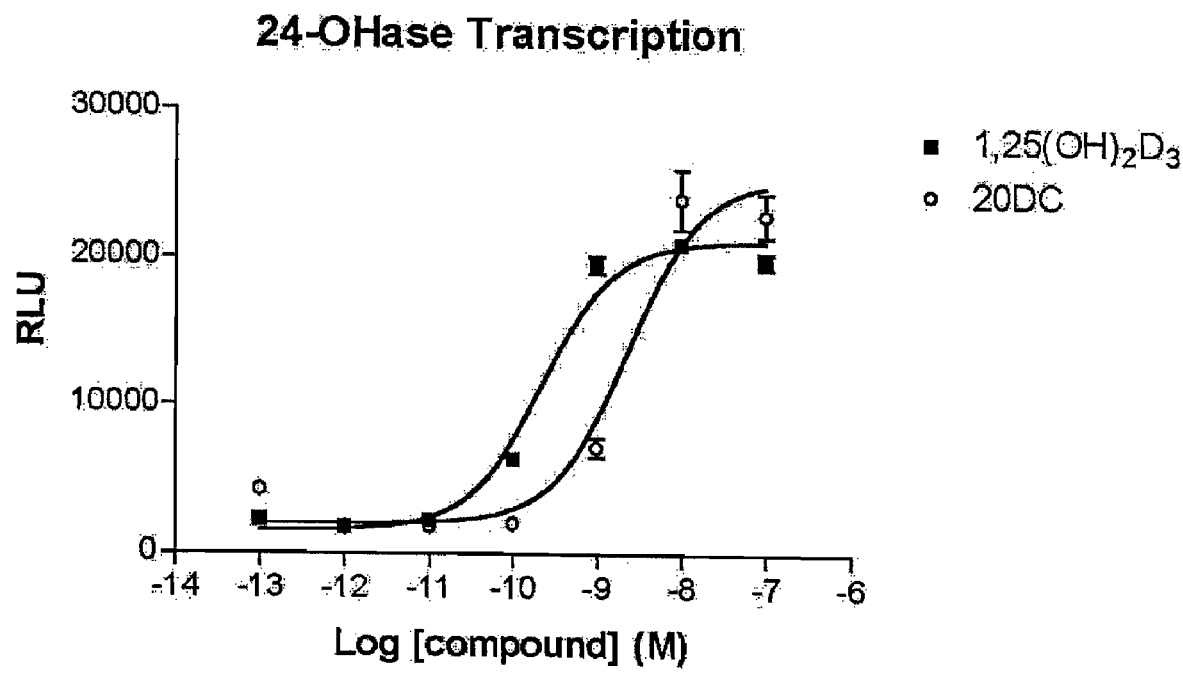

FIG. 3 illustrates that the compound 20DC has about the same transcriptional activity as 1α,25-dihydroxyvitamin $D_3$ in bone cells. This result, together with the cell differentiation activity of FIG. 2, suggests that 20DC will be very effective in psoriasis because it has direct cellular activity in causing cell differentiation, gene transcription, and in suppressing cell growth. These data also indicate that 20DC may have significant activity as an anti-cancer agent, especially against leukemia, colon cancer, breast cancer, skin cancer, lung cancer and prostate cancer.

The strong activity of 20DC on HL-60 differentiation suggests it will be active in suppressing growth of parathyroid glands and in the suppression of the preproparathyroid gene.

Experimental Methods

Vitamin D Receptor Binding
Test Material
Protein Source
Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs
Unlabeled ligands were dissolved in ethanol and the concentrations determined using UV spectrophotometry (1,25$(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25$(OH)_2D_3$,~159 Ci/mmole) was added in ethanol at a final concentration of 1 nM.

Assay Conditions
Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol ($\leq 0.2\%$) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=Relative Luciferase Units.

Intestinal Calcium Transport and Bone Calcium Mobilization

Male, weanling Sprague-Dawley rats were placed on Diet 11 (0.47% Ca) diet +AEK for one week followed by Diet 11 (0.02% Ca) +AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

VDR binding, HL60 cell differentiation, and transcription activity. 20DC ($K_i=8\times10^{-11}$M) is about as active as the natural hormone 1α,25-dihydroxyvitamin $D_3$ ($K_i=9\times10^{-11}$M) in its ability to compete with [$^3$H]-1,25(OH)$_2D_3$ for binding to the full-length recombinant rat vitamin D receptor (FIG. 1). There is also little difference between 20DC ($EC_{50}=5\times10^{-8}$M) in its ability (efficacy or potency) to promote HL60 differentiation as compared to 1α,25-dihydroxyvitamin $D_3$ ($EC_{50}=2\times10^{-8}$M) (See FIG. 2). Also, compound 20DC ($EC_{50}=2\times10^{-9}$M) has similar transcriptional activity in bone cells as 1α,25-dihydroxyvitamin $D_3$ ($EC_{50}=2\times10^{-10}$M) (See FIG. 3). These results suggest that 20DC will be very effective in psoriasis because it has direct cellular activity in causing cell differentiation, gene transcription, and in suppressing cell growth. These data also indicate that 20DC will have significant activity as an anti-cancer agent, especially against leukemia, colon cancer, breast cancer, skin cancer, lung cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of 20DC and 1α,25(OH)$_2D_3$ in intestine and bone were tested. As expected, the native hormone (1,25(OH)$_2D_3$) increased serum calcium levels at the dosage tested (FIG. 4). FIG. 4 shows that 20DC has little, if any, activity in mobilizing calcium from bone. Administration of 20DC at 260 pmol/day for 4 consecutive days did not result in mobilization of bone calcium, and increasing the amount of 20DC to 2340 pmol/day was also without any substantial effect.

Intestinal calcium transport was evaluated in the same groups of animals using the everted gut sac method (FIG. 5). These results show that the compound 20DC does not promote intestinal calcium transport when administered at 260 pmol/day, or 2340 pmol/day, whereas 1,25(OH)$_2D_3$ promotes a significant increase at the 260 pmol/day dose. Thus, it may be concluded that 20DC is essentially devoid of intestinal calcium transport activity at the doses tested.

These results illustrate that 20DC is an excellent candidate for numerous human therapies as described herein, and that it may be particularly useful in a number of circumstances such as suppression of secondary hyperparathyroidism of renal osteodystrophy, autoimmune diseases, cancer, and psoriasis. 20DC is an excellent candidate for treating psoriasis because: (1) it has significant VDR binding, transcription activity and cellular differentiation activity; (2) it is devoid of hypercalcemic liability unlike 1,25(OH)$_2D_3$; and (3) it is easily synthesized. Since 20DC has significant binding activity to the vitamin D receptor, but has little ability to raise blood serum calcium, it may also be particularly useful for the treatment of secondary hyperparathyroidism of renal osteodystrophy.

These data also indicate that the compound 20DC of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound 20DC of the invention.

The compounds of the invention of formula I are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 20DC, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 10 mg per day of the compounds I, particularly 20DC, preferably from about 0.1 µg to about 1 mg per day, is appropriate for prevention and/or treatment purposes, such dose being adjusted according to the disease to be treated, its severity and the response of the subject as is well understood in the art. Since the compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly 20DC, as defined by the above formula I as the active ingredient, and a suitable carrier. An effective amount of such compound for use in accordance with this invention is from about 0.01 µg to about 10 mg per gm of composition, preferably from about 0.1 µg to about 1 mg per gram of composition, and may be administered topically, transdermally, orally or parenterally in dosages of from about 0.01 µg/day to about 10 mg/day, and preferably from about 0.1 µg/day to about 1 mg/day.

The compounds I, particularly 20DC, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 20DC, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

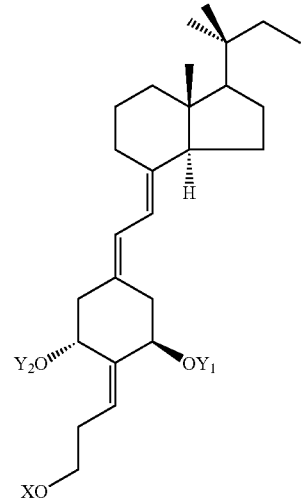

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

2. The compound of claim 1 wherein $Y_1$ is hydrogen.

3. The compound of claim 1 wherein $Y_2$ is hydrogen.

4. The compound of claim 1 wherein $Y_1$ and $Y_2$ are both hydrogen.

5. The compound of claim 1 wherein X is hydrogen.

6. The compound of claim 1 wherein each of $Y_1$ and X is hydrogen.

7. The compound of claim 1 wherein each of $Y_2$ and X is hydrogen.

8. The compound of claim 1 wherein each of $Y_1$, $Y_2$ and X is t-butydimethylsilyl.

9. A pharmaceutical composition containing an effective amount of at least one compound as claimed in claim 1 together with a pharmaceutically acceptable excipient.

10. The pharmaceutical composition of claim 9 wherein said effective amount comprises from about 0.01 µg to about 10 mg per gram of composition.

11. The pharmaceutical composition of claim 9 wherein said effective amount comprises from about 0.1 µg to about 1 mg per gram of composition.

12. 1α-hydroxy-2-[3'-hydroxypropylidene]-20-methyl-19, 24, 25, 26, 27-pentanorvitamin $D_3$ (E-isomer) having the formula:

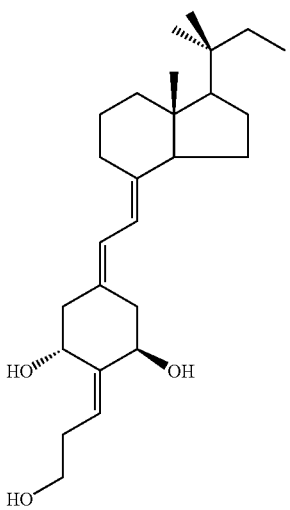

13. A pharmaceutical composition containing an effective amount of 1α-hydroxy -2-[3'-hydroxypropylidene]-20-methyl-19, 24, 25, 26, 27-pentanorvitamin $D_3$ (E-isomer) together with a pharmaceutically acceptable excipient.

14. The pharmaceutical composition of claim 10 wherein said effective amount comprises from about 0.01 µg to about 10 mg per gram of composition.

15. The pharmaceutical composition of claim 10 wherein said effective amount comprises from about 0.1 µg to about 1 mg per gram of composition.

16. A method of treating psoriasis comprising administering to a subject with psoriasis an effective amount of a compound having the formula:

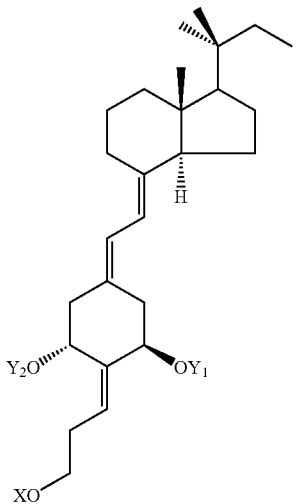

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

17. The method of claim 16 wherein the compound is administered orally.

18. The method of claim 16 wherein the compound is administered parenterally.

19. The method of claim 16 wherein the compound is administered transdermally.

20. The method of claim 16 wherein the compound is administered topically.

21. The method of claim 16 wherein the compound is administered rectally.

22. The method of claim 16 wherein the compound is administered nasally.

23. The method of claim 16 wherein the compound is administered sublingually.

24. The method of claim 16 wherein the compound is administered in a dosage of from about 0.01 µg/day to about 10 mg/day.

25. The method of claim 16 wherein the compound is 1α-hydroxy-2-[3'-hydroxypropylidene]-20-methyl-19, 24, 25, 26, 27-pentanorvitamin $D_3$ (E-isomer) having the formula:

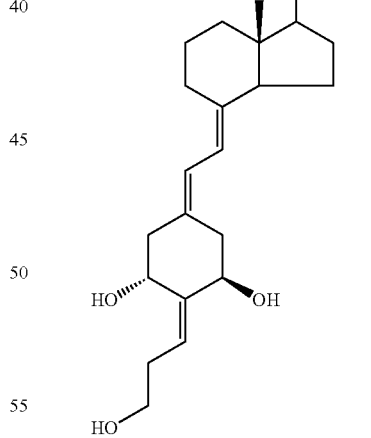

26. A method of treating a disease selected from the group consisting of leukemia, colon cancer, breast cancer, skin cancer, lung cancer, or prostate cancer comprising administering to a subject with said disease an effective amount of a compound having the formula:

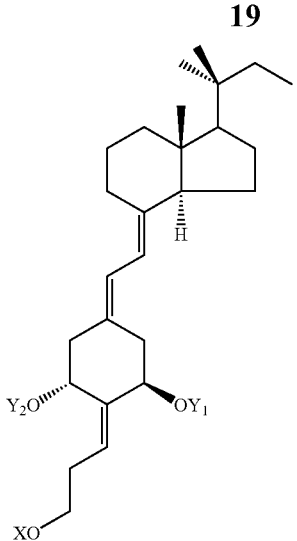

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

27. The method of claim 26 wherein the compound is administered orally.

28. The method of claim 26 wherein the compound is administered parenterally.

29. The method of claim 26 wherein the compound is administered transdermally.

30. The method of claim 26 wherein the compound is administered rectally.

31. The method of claim 26 wherein the compound is administered nasally.

32. The method of claim 26 wherein the compound is administered sublingually.

33. The method of claim 26 wherein the compound is administered in a dosage of from about 0.01 μg/day to about 10 mg/day.

34. The method of claim 26 wherein the compound is 1α-hydroxy-2-[3'-hydroxypropylidene]-20-methyl-19, 24, 25, 26, 27-pentanorvitamin $D_3$ (E-isomer) having the formula:

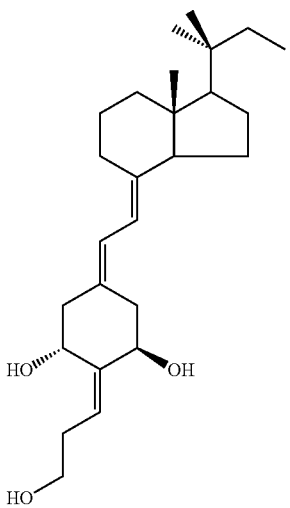

35. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

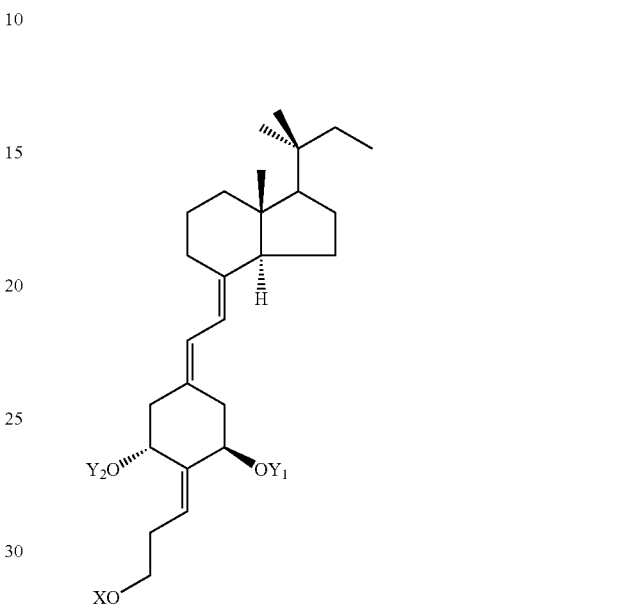

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

36. The method of claim 35 wherein the compound is administered orally.

37. The method of claim 35 wherein the compound is administered parenterally.

38. The method of claim 35 wherein the compound is administered transdermally.

39. The method of claim 35 wherein the compound is administered rectally.

40. The method of claim 35 wherein the compound is administered nasally.

41. The method of claim 35 wherein the compound is administered sublingually.

42. The method of claim 35 wherein the compound is administered in a dosage of from about 0.01 μg/day to about 10 mg/day.

43. The method of claim 35 wherein the compound is 1α-hydroxy-2-[3'-hydroxypropylidene]-20-methyl-19, 24, 25, 26, 27-pentanorvitamin $D_3$ (E-isomer) having the formula:

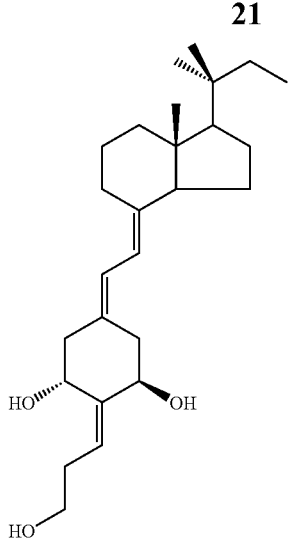

44. A method of treating an inflammatory disease selected from the group consisting of rheumatoid arthritis, asthma, and inflammatory bowel diseases, comprising administering to a subject with said disease an effective amount of a compound having the formula:

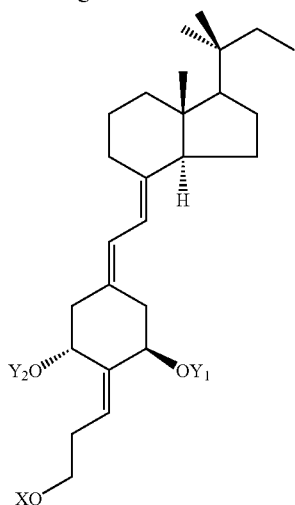

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

45. The method of claim 44 wherein the compound is administered orally.
46. The method of claim 44 wherein the compound is administered parenterally.
47. The method of claim 44 wherein the compound is administered transdermally.
48. The method of claim 44 wherein the compound is administered rectally.
49. The method of claim 44 wherein the compound is administered nasally.
50. The method of claim 44 wherein the compound is administered sublingually.
51. The method of claim 44 wherein the compound is administered in a dosage of from about 0.01 µg/day to about 10 mg/day.
52. The method of claim 44 wherein the inflammatory bowel disease is celiac disease.
53. The method of claim 44 wherein the inflammatory bowel disease is ulcerative colitis.
54. The method of claim 44 wherein the inflammatory bowel disease is Crohn's disease.
55. The method of claim 44 wherein the compound is 1α-hydroxy-2-[3'-hydroxypropylidene]-20-methyl-19, 24, 25, 26, 27-pentanorvitamin $D_3$ (E-isomer) having the formula:

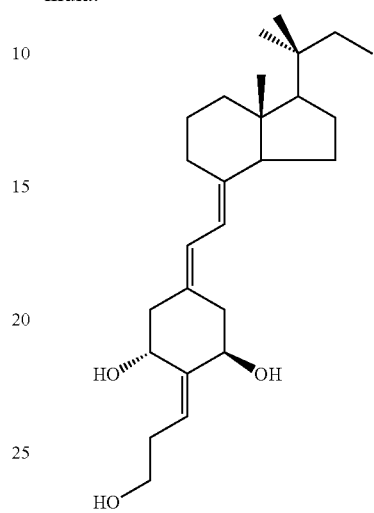

56. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

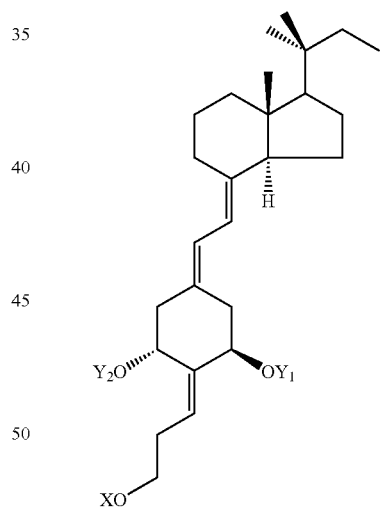

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

57. The method of claim 56 wherein the compound is administered orally.
58. The method of claim 56 wherein the compound is administered parenterally.
59. The method of claim 56 wherein the compound is administered transdermally.
60. The method of claim 56 wherein the compound is administered topically.

61. The method of claim 56 wherein the compound is administered rectally.

62. The method of claim 56 wherein the compound is administered nasally.

63. The method of claim 56 wherein the compound is administered sublingually.

64. The method of claim 56 wherein the compound is administered in a dosage of from about 0.01 µg/day to about 10 mg/day.

65. The method of claim 56 wherein the compound is 1α-hydroxy-2-[3'-hydroxypropylidene]-20-methyl-19, 24, 25, 26, 27-pentanorvitamin $D_3$ (E-isomer) having the formula:

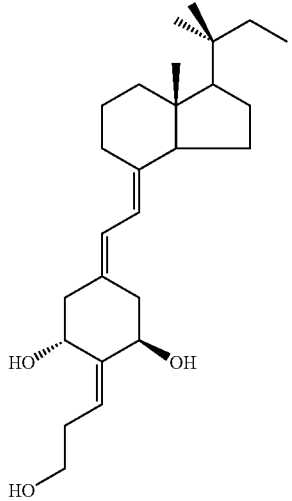

66. A method of treating renal osteodystrophy comprising administering to a subject with renal osteodystrophy an effective amount of a compound having the formula:

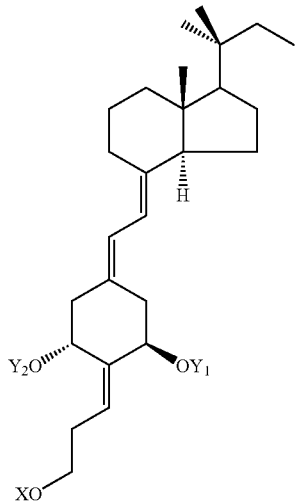

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

67. The method of claim 66 wherein the compound is administered orally.

68. The method of claim 66 wherein the compound is administered parenterally.

69. The method of claim 66 wherein the compound is administered transdermally.

70. The method of claim 66 wherein the compound is administered rectally.

71. The method of claim 66 wherein the compound is administered nasally.

72. The method of claim 66 wherein the compound is administered sublingually.

73. The method of claim 66 wherein the compound is administered in a dosage of from about 0.01 µg/day to about 10 mg/day.

74. The method of claim 66 wherein the compound is 1α-hydroxy-2-[3'-hydroxypropylidene]-20-methyl-19, 24, 25, 26, 27-pentanorvitamin $D_3$ (E-isomer) having the formula:

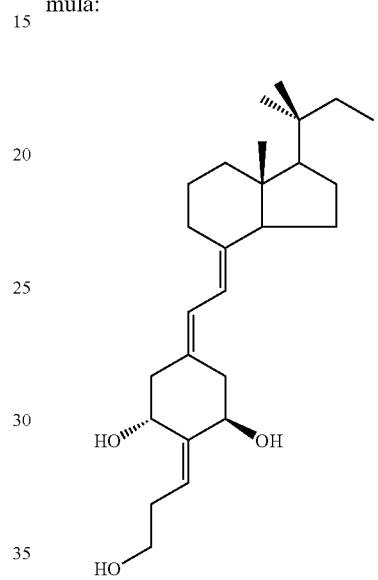

75. A method of treating obesity of an animal, inhibiting adipocyte differentiation, inhibiting SCD-1 gene transcription and/or reducing body fat in an animal comprising administering to an animal in need thereof an effective amount of a compound having the formula:

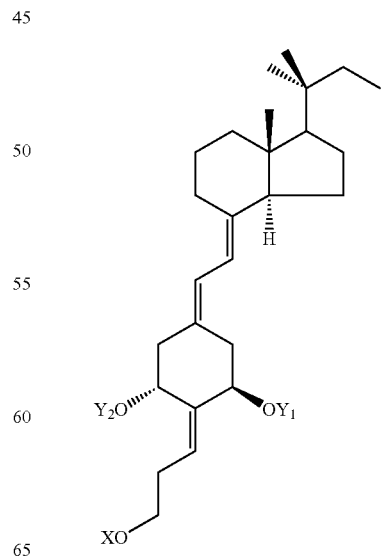

where $Y_1$ and $Y_2$, which may be the same or different, are each selected from the group consisting of hydrogen and a hydroxy-protecting group, and where X is selected from the group consisting of an alkyl, a hydrogen, a hydroxy-protecting group, a hydroxyalkyl, an alkoxyalkyl and an aryloxyalkyl.

76. The method of claim 75 wherein the compound is administered orally.

77. The method of claim 75 wherein the compound is administered parenterally.

78. The method of claim 75 wherein the compound is administered transdermally.

79. The method of claim 75 wherein the compound is administered rectally.

80. The method of claim 75 wherein the compound is administered nasally.

81. The method of claim 75 wherein the compound is administered sublingually.

82. The method of claim 75 wherein the compound is administered in a dosage of from about 0.01 μg/day to about 10 mg/day.

83. The method of claim 75 wherein the compound is 1α-hydroxy-2-[3'-hydroxypropylidene]-20-methyl-19, 24, 25, 26, 27-pentanorvitamin $D_3$ (E-isomer) having the formula:

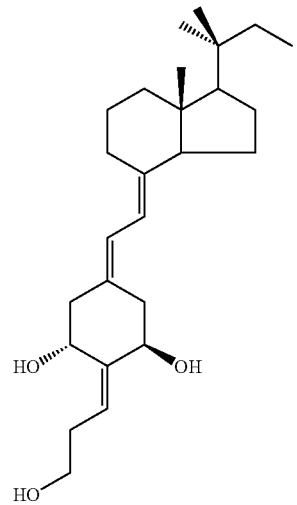

84. The method of claim 75 wherein the animal is a human.

85. The method of claim 75 wherein the animal is a domestic animal.

86. The method of claim 75 wherein the animal is an agricultural animal.

* * * * *